United States Patent [19]

Hiraga et al.

[11] 4,020,269

[45] Apr. 26, 1977

[54] EPIMINODEAMINODEOXYAMINOGLYCO-SIDE ANTIBIOTICS AND INTERMEDIATES

[75] Inventors: Kentaro Hiraga, Kyoto; Tetsuya Okutani, Osaka; Tsunehiko Asako; Kouichi Yoshioka, both of Kyoto, all of Japan

[73] Assignee: Takeda Chemical Industries, Ltd., Osaka, Japan

[22] Filed: Apr. 8, 1975

[21] Appl. No.: 566,519

[30] Foreign Application Priority Data

Apr. 10, 1974 Japan .............................. 49-41367
Apr. 10, 1974 Japan .............................. 49-41368
June 25, 1974 Japan .............................. 49-72945

[52] U.S. Cl. ................................. 536/10; 424/180; 536/12; 536/17
[51] Int. Cl.² ....................................... C07H 15/22
[58] Field of Search ............. 260/210 AB, 210 NE, 260/210 K; 536/10, 12, 17

[56] References Cited

UNITED STATES PATENTS 3,753,973  8/1973  Umezawa et al. ........... 260/210 AB
3,868,360  2/1975  Daniels et al. ............. 260/210 AB

OTHER PUBLICATIONS

Umezawa et al., "Jour. of Antibiotics", vol. XXVI, No. 7, 1973, pp. 407–410.
Umezawa et al., "Jour. of Antibiotics", vol. XXVI, No. 12, 1973, pp. 799–800.

*Primary Examiner*—Johnnie R. Brown
*Attorney, Agent, or Firm*—Wenderoth, Lind & Ponack

[57] ABSTRACT

Deoxyaminoglycoside antibiotics are prepared in a high yield from phosphorylated aminoglycosides by reacting a phosphorylated aminoglycoside (a) with a silylating agent, or (b) successively with (i) a silylating or acylating agent and (ii) a halogenating agent; then subjecting thus obtained intermediate to reduction. Deoxyaminoglycoside antibiotics are useful for treating infections caused by microorganisms which are resistant or non-resistant to the corresponding aminoglycoside antibiotics.

12 Claims, No Drawings

EPIMINODEAMINODEOXYAMINOGLYCOSIDE ANTIBIOTICS AND INTERMEDIATES

This application dicloses some of the same subject matter disclosed in Ser. No. 426,693, filed Dec. 20, 1973.

This invention relates to novel processes of dehydroxylation of aminoglycoside antibiotics.

Hitherto, aminoglycoside antibiotics have widely been used for treating infections caused by microorganisms in human and animal therapies. But, as the result of the administration of the antibiotics, a number of microorganisms resistant to the antibiotics have appeared.

Recently, there have been reports that deoxyaminoglycoside antibiotics are effective against these aminoglycoside antibiotic-resistant microorganisms. As to dehydroxylation of aminoglycoside anitbiotics, for instance, Journal of Antibiotics 21, 613–616(1972) reports that 3',4'-dideoxyribostamycin is synthesized starting from ribostamycin through nine steps with at most 15% overall yield. Such synthesis is, of course, not necessarily an industrially feasible process.

Under these circumstances, the present inventors have made an extensive study for finding an efficient process for dehydroxylation of aminoglycoside antibiotics, which culminated in the discovery of novel processes for dehydroxylation of aminoglycoside antibiotics.

Thus, it is an object of this invention to provide an entirely new route for dehydroxylation of aminoglycoside antibiotics. Another object of this invention is to provide a new method for the production of dehydroxylated aminoglycoside antibiotics in a high field. A further object of this invention is to provide new intermediates which are effective against aminoglycoside antibiotic-resistant microorganisms.

Thus, this invention relates to a method for the production of deoxyaminoglycoside antibiotics which comprises reacting a phosphorylated aminoglycoside (a) with a silylating agent, or (b) successively with (i) a silylating or acylating agent and (ii) a halogenating agent (Step 1), then subjecting thus obtained intermediate to reduction (Step 2).

The aminoglycoside antibiotics include neomycin type aminoglycoside antibiotics which have sugars at 4- and/or 5-position(s) of 2-deoxystreptamine such as neomycins (e.g. neomycin A, neomycin B, neomycin C, neomycin LPb, neomycin (LPc), paromomycins (e.g. paromomycin I, paromomycin II), butirosins (e.g. butirosin A, butirosin B, butirosin 1709E$_1$, butirosin 1709E$_2$), ribostamycin, xylostasin, lividomycins (e.g. lividomycin A, lividomycin B) or of streptamine such as hybrimycins (e.g. hybrimycin A$_1$, hybrimycin A$_2$, hybrimycin A$_3$, hybromycin B$_1$, hybrimycin B$_2$, hybrimycin B$_3$), kanamycin type aminoglycoside antibiotics which have sugars at 4- and 6-positions of 2-deoxystreptamine such as kanamycins (e.g. kanamycin A, kanamycin B, kanamycin C), 3',4'-dideoxykanamycin B, gentamycins (e.g. gentamycin C$_{1a}$, gentamycin C$_1$, gentamycin C$_2$, gentamycin A, gentamycin B, gentamycin B$_1$, gentamycin X, tobramycin, sisomicin, streptomycin type aminoglycoside antibiotics such as streptomycins (e.g. streptomycin, streptomycin B, dihydrostreptomycin, dihydrodesoxystreptomycin), hydroxystreptomycin, bluensomycin, and other aminoglycoside type antibiotics such as destomycins (e.g. destomycin A, destomycin B), hygromycin B, trehalosamine, mannosilglucosamine, actinospectasin.

The term "deoxyaminoglycoside antibiotic" means a compound derived by dehydroxylation of the starting aminoglycoside antibiotic. Therefore, the starting aminoglycoside antibiotics include deoxyaminoglycoside antibiotics as such, for example, monodeoxyaminoglycoside antibiotics, dideoxyaminoglycoside antibiotics.

In the present invention phosphorylated aminoglycoside antibiotics are employed as starting materials. The phosphate ester residue is, for example, the ester of phosphoric acid, nucleotidyl phosphoric acid (e.g. adenylic acid, guanylic acid, cytidylic acid, uridic acid, inosinic acid), alkylphosphoric acid (e.g. dimethylphosphoric acid, diethylphosphoric acid, methylphosphoric acid). The phosphorylated aminoglycoside antibiotics are obtained by phosphorylation of the corresponding aminoglycoside antibiotics.

The phosphorylation of the aminoglycoside antibiotics is conducted by, for example, bringing the aminoglycoside antibiotics into contact with a culture broth or an enzyme, or phosphotransferase, of a microorganism belonging to, for example, *Pseudomonas aeruginosa* or *Escherichia coli* in the presence of a phosphate donor. (see Reference Examples 2, 3 and 4) The typical examples of the said microorganism are *Escherichia coil* R11 (FERM-P No. 2123, IFO-13560, ATCC-21990), *Bacillus vitellinus* Z-1159 (FERM-P No. 1203, IFO-13296, ATCC-31078), *Escherichia coili* K12 ML 1629 (Journal of Antibiotics, 21, No. 1, 22–29(1968)), *Escherichia coli* ML 1401 Rm$_{81}$+ (Antimicrobial Agents and Chemotherapy, 2, No. 3, 142–146 (1972)) and *Escherichia coil* JR66/W677 (FEBS LETTERS 14, No. 5, 293 (1971)). The numbers in the parenthesis attached to the above strain and indicated by FERM-P, IFO, ATCC are the accession numbers at the Fermentation Research Institute of the Agency of Industrial Science and Technology, Chiba, Japan (FERM); the Institute for Fermentation, Osaka, Japan (IFO); and the American Type Culture Collection (ATCC); respectively. The typical examples of phosphate donor are adenosine triphosphate, adenosine diphosphate, deoxyadenosine triphosphate, deoxyadenosine diphosphate, cytidinetriphosphate, guanosinetriphosphate and uridinetriphosphate. By phosphorylation, one or more hydroxyl groups of aminoglycoside antibiotics are phosphorylated. The phosphorylated hydroxyl group is sometimes referred to as "phosphonoxy group" hereinafter. Positions of phosphonoxy groups vary with the types of aminoglycoside antibiotics and phosphorylation conditions, especially, kinds of phosphotransferase employed. The phosphonoxy group includes unsubstituted phosphonoxy group ($-OPO_3H_2$), substituted phosphonoxy groups such as nucleotidylphosphonoxy groups (e.g. adenosylphosphonoxy, uridylphosphonoxy, 5'-inosinylphosphonoxy, 5'-guanosylphosphonoxy), alkylphosphonoxy groups (e.g. dimethylphosphonoxy, diethylphosphonoxy, methylphosphonoxy, ethylphosphonoxy). Separation of the phosphorylated aminoglycoside antibiotics thus obtained from the reaction mixture is conducted by a per se conventional manner such as extraction, precipitation, lyophylization and column chromatography with a column packed with ion-exchange resin, ion-exchange cellulose or activated carbon.

A detailed explanation of the steps of the processes of the present invention is given below.

Step 1

In the first step of the present process, a phosphorylated aminoglycoside is (a) reacted with a silylating agent (Step 1-(A)), or (b) reacted with (i) a silyating or acylating agent and (ii) a halogenating agent (Step 1-(B)).

Step 1-(A)

First, the phosphorylated aminoglycoside antibiotic is allowed to react with a silyating agent. The silylating agent is exemplified by halosilanes (e.g. trimethylsilylchloride, trimethylsilylbromide, trimethylsilyliodide, dimethylphenylsilylchloride, dimethyl-t-butylsilylchloride, dimethyldichlorosilane, chloromethyldimethylchlorosilane, bromomethyldimethylchlorosilane, trichlorosilane, triphenylsilylchloride, etc.), silyl compounds of amines (e.g. hexamethyldisilazane, N-trimethylsilyldimethylamine, N-trimethylsilyl-t-butylamine, N-trimethylsilyldiethylamine, etc.), bissilyl compounds of carboxylic acid amide [e.g. bis(trimethylsilyl)acetamide, bis(trimethylsilyl)trifluoroacetamide, bis(trimethylsilyl)propionamide, etc.], monosilyl compounds of carboxylic acid amide (e.g. N-trimethylsilylacetamide, N-methyl-N-trimethylsilylacetamide, N-ethyl-N-trimethylsilylacetamide, N-trimethylsilyl pyridone, N-trimethylsilyl pyrrolidone, etc.), silyl derivatives of imidazole (e.g. trimethylsilylimidazole, trimethylsilyl-2-methylimidazole, etc.), a mixture of trialkylsilane (e.g. trimethylsilane, triethylsilane, etc.) or dialkylarylsilane (e.g. dimethylphenylsilane, etc.) and a metal catalyst [e.g. Willkinson complex (tris-(triphenylphosphine)rhodium chloride), palladium chloride, zinc chloride, etc.)] and a mixture of not less than two kinds of these silyating agents. The amount of the silylating agent used may be 10 to 500 moles, preferably 50 to 200 moles per mole of the starting phosphorylated aminoglycoside. The silylating reaction may be conducted in a solvent, preferably in a non-protonating solvent such as pyridine, benzene, toluene, xylene, dioxane, tetrahydrofuran, dimethylformamide, hexamethylphosphoric triamide, hexamethylphosphorus triamide, acetonitrile. The reaction is more smoothly conducted in the presence of a phosphine (e.g. tri-arylphosphines such as triphenylphosphine, trialkylphosphines such as tri-n-butylphosphine) or metal halides (e.g. zinc chloride, lithium chloride, aluminium chloride, titanium chloride, tin chloride, antimony chloride, boron trifluoride). The reaction advantageously proceeds under heating, and the heating temperature is from about 50° to about 200° C, preferably from about 80° to about 150° C.

The production of epiminodeaminodeoxyaminoglycoside in the Step 1-(A) is conducted by employing a phosphorylated aminoglycoside which has the following partial structure:

i. Phosphonoxy group is bound with secondary carbon atom,
ii. This secondary carbon atoms is bound with a carbon atom having a primary or secondary amino group, and
iii. The amino group and the phosphonoxy group take the trans-configuration to each other, namely the structure

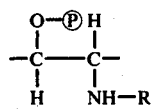

wherein $-O-\text{P}$ is phosphonoxy group and $-NH-R$ is primary or secondary amino group. And the epiminodeaminodeoxyaminoglycoside had the following partial structure (aziridine ring) in the corresponding part;

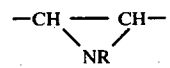

wherein R has the same meaning as above.

The said aziridine ring is preferably located at 2' and 3'-positions in the aminoglycoside compound.

Step 1-(B)

Alternatively, the starting phosphorylated aminoglycoside antibiotic is reacted with (i) a silylating or acrylating agent, and with (ii) a halogenating agent. The silylating agent employed in this step may, for example, be hexamethyldisilazane, trimethylchlorosilane, bis(trimethylsilyl) acetamide, bis(trimethylsilyl)-trisfluoroacetamide, trimethylsilylacetamide, N-methyl-N-trimethylsilylacetamide, N-trimethylsilylimiazole, N(trimethylsilyl)diethylamine or halosilane (e.g. dimethyldichlorosilane). When the silylating agent is used, the reaction need not necessarily be conducted in a solvent, though a non-protonating solvent may be employed. The non-protonating solvent may, for example, be pyridine, benzene, dimethylformamide, tetrahydrofuran, dioxane, acetonitrile or hexamethylphosphoramide. If desired, the reaction may be caused to proceed more adantageously by employing a tertiary amine, e.g. triethylamine, pyridine, diisopropylmethylamine, triethylenediamine, as a catalyst. This silylating reaction is carried out at about −50° C to about 200° C and, preferably, at 0° C to 150° C. The required amount of the silylating agent is not more than the amount necessary for protecting all the functional group (e.g. hydroxy, amino and guanidino groups), of the starting compound, though an excess of the agent may be employed.

In place of silyl groups the starting compund is reacted with an acylating agent such acetic anhydride, acetyl chloride, benzoyl chloride. This reaction may be conducted in a solvent, siuch as pyridine, collidine, dimethylformamide, acetonitrile, hexamethylphosphoramide, and in the presence of a base as a catalyst. The base may, for example, be triethylamine, triethylenediamine or pyridine. This reaction is conducted at −50° C to 200° C, preferably at 80° C to 150° C. The amount of the acylating agent may be not more than the amount required for protecting all the functional groups of the starting compound, although it may be used in excess.

The above silylating and acylating agents may also be used in combination or reacted one after the other so that they will be introduced into the functional groups of the starting compound.

Then, the resulting phosphorylated and protected aminoglycoside is reacted with a halogenating agent. The halogenating agent includes halosilanes, for example, trialkylsilyl halide (e.g. trimethylsilychloride, dimethyl-t-butylsilyl chloride, trimethylsilyl bromide, dimethyldichlorosilane, trimethylsilyl iodide), triarylsilyl halide (e.g. triphenylsilyl chloride), arylalkylsilyl halide (e.g. phenyldimethylsilyl chloride, methyldiphenylsilyl chloride), trialkoxysilyl halide (e.g. trimethoxysilyl chloride, triethoxysilyl chloride), thionyl chloride, pyridinium chloride, pyridinium bromide, trimethoxymethylphosphonium iodide, phosphorus oxychloride, phosphorus thiooxychloride, phosphorus pentachloride, oxalyl chloride, phosphorus pentabromide and so on. The amount of halogenating agent may be equimolar to the compound obtained by the reaction just described, although usually an excess of the agent is employed. One may use a mixture of such agents. This reaction is conducted at from $-50°$ to $200°$ C and, for better results, at from $80°$ to $150°$ C. While the reaction may be conducted in the absence of a solvent, a non-protonating solvent may be employed, if desired. The non-protonating solvent may, for example, by pyridine, benzene, dimethylformamide, tetrahydrofuran, dioxane, hexamethylphosphoramide or acetonitrile. The reaction may be conducted more smoothly in the presence of a phosphine (for example, triarylphosphine (e.g. triphenylphosphine), trialkylphosphine (e.g. tri-n-butylphosphine)), metal halide (e.g. zinc chloride, lithium chloride, aluminum chloride, boron trifluoride, titanium chloride) or a mixture thereof. Among these halogenating agents halosilanes double as the halogenating agent and the protecting agent. The halogenation proceeds very smoothly when the phosphorylated aminoglycoside has the following structural characteristics:

i. Phosphonoxy group is bound with secondary carbon atom.
ii. This secondary carbon atom is bound with a carbon atom having a primary or secondary amino group, and
iii. The amino group and the phosphonoxy group take the trans-configuration to each other, or when the phosphorylated aminoglycoside has the phosphonoxy group which is bound with primary carbon atom. The said phosphorylated aminoglycoside may be typically exemplified by neomycin type antibiotics having phosphonoxy groups(s) at 3'- and/or 5'''-positions, kanamycin type antibiotics having the phosphonoxy groups at 3'- and/or 2''-position(s) and streptomycin type antibiotics having phosphonoxy group at 3''-position. The halogenation gives a halogenated aminoglycoside antibiotic having the following structural configuration:

i. Halogen atom is bound with a secondary carbon atom,
ii. This secondary carbon atom is bound with a carbon atom having a primary or secondary amino group or one having the halogen atom bound with a primary carbon atom. Halogen is chlorine, bromine, fluorine and iodine.

The above finding regarding the halogenation was made by the present invention for the first time and this finding is to be applicable to halogenation of all the amino glycoside compounds.

In Step 1 of the present process, epiminodeaminodeoxy aminoglycosides are mainly produced in the reaction of Step 1-(A), whereas halogenodeoxyaminoglycosides are mainly produced in the reaction of Step 1-(B) and if desired, these intermediates can be purified by the per se conventional method such as de-salt with ion-exchange resin and column chromatography.

Said epiminodeaminodeoxyaminoglycosides and halogenodeoxyaminoglycosides are useful as intermediates for producing deoxyaminoglycosides and also useful as antibiotics effective against not only when microorganisms but also aminoglycoside antibiotic-resistant microorganisms.

Following the Step 1 above, the resultant product is subjected to the reaction of Step 2. The starting material of Step 2 may be either epiminodeaminodeoxyaminoglycoside or halogenodeoxyaminoglycoside, or, as the case may be, a mixture of them. Further, the starting material may still have a silyl group and/or an acyl group having been introduced in the molecule through Step 1.

Step 2

The products of the Step 1 are then subjected to reduction. The reduction is conducted by the manner per se known, such as catalytic reduction, electrolytic reduction, reduction using a reducing agent and reduction using a Grignard reagent.

When the reduction is practiced by catalytic reduction, i.e. by reduction in the presence of a catalyst, the following procedure may be followed. Thus, the starting material is first dissolved in a routine solvent such as water, alcohols (e.g. methanol, ethanol, isopropanol, etc.), acetone, dioxane, tetrahydrofuran, dimethylformamide or their mixture and hydrogen gas is bubbled into the solution in the presence of a catalyst (e.g. Raney nickel, palladium-on-carbon, palladium-barium carbonate, platinum oxide, rhodium complex, Raney type catalyst of cobalt, Raney type catalyst of iron, Raney type catalyst of copper). This reaction is carried out at a temperature of from $-30°$ C to $150°$ C, desirably at from room temperature of $100°$ C. While the reaction proceeds readily at atmospheric pressure, one may conduct it at an elevated pressure between 5 and 100 kg/cm². The reaction may be hastened and, depending upon the particular type of starting intermediate compound, the yield of the objective product may be enhanced by adding a suitable base to the reaction system, examples of said base including triethylamine, diethylamine ad alkali metal hydroxide.

When electrolytic reduction is used, the starting material is dissolved in a suitable solvent and, then, the routine procedure is applied. For example, the compound is dissolved in a solvent (e.g. water, alcohol (e.g. methanol, ethanol, etc.), ammonia, dimethylformamide, etc.) and the reduction is carried out using a low overvoltage electrode (e.g. platinum, wolfram, etc.) or a high overvoltage electrode (e.g. lead, zinc, mercury, etc.). Better results are sometimes obtained when the pH of the solution is brought to the acid side, for example to ph 2–3.

When the reduction is to be practiced employing a reducing agent, the starting material is treated with a reducing agent, for example, a metal hydride (e.g. lithium aluminum hydride, sodium aluminum hydride, sodium borohydride, tributyltin hydride, tributylzinc hydride), alkali metal (e.g. lithium, sodium), a metal salt (e.g. divalent chromium salts such as chromas chloride, chromous acetate), zinc, amalgamated zinc, alinium amalgam. The reaction is conducted in a suitable solvent such as alcohols (e.g. methanol, ethanol, propanol, iso-propanol, butanol, amylalcohol, isoamyl alcohol), ethers (e.g. ethylether, dioxane, tetrahydrofuran), dimethylformamide, dimethylsulfoxide, ethylene glycol, ethylenediamine, diethylenetriamine, glyme, diglyme). The reaction is conducted at a temperature of $-30°$ to $150°$ C, and preferably at room temperature to $80°$ C.

When a Grignard reagent is employed, the following procedure is followed. Thus, the starting material is treated with magnesium metal in a solvent which is routinely used in Grigard reactions, e.g. tetrahydrofuran, ether or dioxane, and the resultant Grignard reagent is decomposed with water, methanol, ethanol, n-butanol or the like at room temperature or, if required, under heating.

The silylation reaction in Step 1 gives a compound whose hydroxy, amino and guanidino group are concomitantly silylated; and the acylation reaction in Step 1 gives a compound whose hydroxy, amino and guanidino group are concomitantly acylated. Such silyl and acyl groups may be released in an optional step of the successive steps. The release of the silyl group may be made by bringing the compound into contact with a proton donor such as water, alcohols (e.g. methyl alcohol, ethyl alcohol), carboxylic acids (e.g. acetic acid, propionic acid), sulfonic acids (e.g. p-toluensulfonic acid), or by reacting the compound with mineral acids (e.g. hydrochloric acid, sulfuric acid). The release of the acyl groups may be made by hydrolyzing the product with, by way of a catalyst, an acid (e.g. hydrochloric acid, sulfuric acid) or an alkali (e.g. sodium hydroxide, barium hydroxide, potassium hydroxide).

Some of the deoxyaminoglycoside antibiotics obtainable by the method of this invention are per se known compounds, but at least the following is a new compound: 3'-deoxyxylostasin, i.e. 0-$\beta$-D-xylofuranosyl-(1 → 5)-0-[$\alpha$-2,6-diamino-2,3,6-trideoxy-D-Glucopyranosyl (1 → 4)]-2-deoxystreptamine.

Separation and purification of the desired deoxyaminoglycoside antibiotics can be conducted by per se routine procedure such as extraction, precipitation, lyophylization, ion-exchange column chromatography on a weakly acid resin.

The objective compound of the present invention can form an acid addition salt by treating it with a suitable acid by per se conventional means. As the acid, they may be, for example, an inorganic acid (e.g. hydrochloric acid, sulfuric acid, nitric acid, phosphoric acid), an organic acid (e.g. trifluoro acetic acid, tartaric acid). Among the said acids, sulfuric acid is more preferable.

The epiminodeaminodeoxyaminoglycoside, halogenodeoxyaminoglycoside and deoxyaminoglycoside antibiotics have substantially the same antibacterial activities as those of the corresponding aminoglycoside antibiotics, and besides they are effective against those bacteria which are resistant to the aminoglycoside antibiotics, and therefore lend themselves to use the treatment of the diseases caused by the bacteria. Typical uses of the present antibiotics are anti-tuberculotics, anti-dysenterics, anti-staphylococcal drugs, drugs fo the treatment of the diseases caused by Pseudomonas or Escherichia.

The epiminodeoxyaminoglycoside, halogenodeoxyaminoglycoside and deoxyaminoglycoside antibiotics may be usually administered in such dosage forms as tablets, injections and so on together with pharmaceutically acceptable carriers in the daily routine dosage of 1 to 30 mg./ kg. to mammal, e.g. human being, bovine, pig or rat. For example, 3'-deoxybutirosin A is used in a form of tablets in the daily routine dosage of about 4 mg./kg., and 3'-deoxyxylostasin is used in a form of injections in the daily routine dosage of about 20 mg./kg. per mammal.

For further explanation of the present invention, the following examples are given, wherein "part(s)" are based on weight unless otherwise noted and the relationship between "part(s)" and "part(s) by volume" corresponds to that between "grams(s)" and "milliliter(s)". The terms "M", "N" and "%" mean molar concentration, normality or equivalent concentration and percent, respectively. Resins named "Amberlite" are products manufactured by Rohm and Haas Company, Ltd. in U.S.A.

REFERENCE EXAMPLE 1

Production of xylostasin by chemical process

In 250 parts by volume of an 0.5N aqueous solution of barium hydroxide is dissolved 5.0 parts of butirosin A. The solution is refluxed for 2 hours and then cooled. The solution is neutralized with 1N sulfuric acid. The resulting precipitate of barium sulfate is removed off by centrifuge. The supernatant fluid is run onto a column of 300 parts by volume of cation exchange resin [Amberlite CG-50 ($NH_4^+$-form) (Rohm and Haas Co.)]. The column is washed with water and eluted with 0.2N aqueous ammonia. Fractions containing xylostasin which is detected by thin layer chromatography are pooled and concentrated under reduced pressure to dryness and lyophilized, whereby 3.8 parts of xylostasin as white powders are obtained.

Elemental analysis for $C_{17}H_{34}N_4O_{10}$; Found: C, 44.23; H, 7.53; N, 12.10; Calculated: C, 44.93; H, 7.54; N, 12.33.

Optical rotation: $[\alpha]_D^{21}=+34°(c=1$ in water).

The chemical name of xylostasin is 0-$\beta$-D-xylofuranosyl-(1 → 5)-0-[$\alpha$-2,6-diamino-2,6-diodeoxy-D-glucopyranosyl(1 → 4)]-2-deoxystreptamine and the chemical structure of xylostasin is as follows;

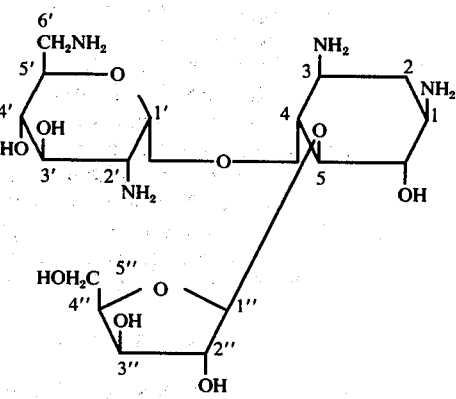

REFERENCE EXAMPLE 2

Phospholylation of xylostasin

Two hundred parts by volume of an aqueous seed culture medium (pH 7.2) comprising 0.5% of yeast extract, 0.5% of polypepton, and 0.3% of meat extract is inoculated with Escherichia coli Rll (IFO-13560). The cultivation is carried out under shaking at 37° C for 16 hours. This seed culture is then inoculated to an aqueous main culture medium (1,800 parts by volume, pH 7.2) having the same composition as the above and the cultivation is carried out under shaking at 37° C for 4 hours. The culture broth is subjected to centrifuge to recover 4.4 parts of wet cells. The cells are suspended into 17.6 parts by volume of 0.05M phosphate buffer (pH 7.0).

The suspension is subjected to ultrasonic oscillation (Kaijo Denki Co., Ltd. T-A-4201, 4280-type, 2A) to disintegrate the cells, followed by removing the debris (insoluble materials) by centrifugation, whereby 17 parts by volume of crude enzyme solution is obtained.

To 17 parts by volume of the crude enzyme solution are added 5 parts of xylostasin, 50 parts by volume of 0.5M phosphate buffer (pH 7.0), 100 parts by volume of 1M adenosine triphosphate solution, 50 parts by volume of 0.1M magnesium acetate solution and 50 parts by volume of 0.1M 2-mercapto ethanol, which is filled up to 500 parts by volume with distilled water. The mixture is subjected to enzymic reaction at 37° C for 20 hours.

The reaction mixture is heated at 80° C for 5 minutes to cease the reaction, followed by centrifuge. The supernatant is run onto a column of 900 parts by volume of cation exchange resin [Amberlite IRC-50($NH_4^+$-form)]. The column is washed with water and eluted with 1N aqueous ammonia to give fractions which contain xylostasin-3'-phosphate. The fractions are collected and concentrated and run onto a column of 150 parts by volume of cation exchange resin [Amberlite CG-50($NH_4^+$-form)].

The column is washed with water, and is fractionated by the linear gradient elution with 1,200 parts by volume of distilled water and 1,200 parts by volume of 0.2N aqueous ammonia. Fractions which include xylostasin-3'-phosphate are collected, concentrated under reduced pressure and lyophilized, whereby 4.4 parts of xylostasin-3'-phosphate monohydrate is obtained as a white powder.

Elemental analysis for $C_{17}H_{35}N_4O_{13}P \cdot H_2O$; Calcd.: C, 36.96; H, 6.75; N, 10.14; P, 5.61; Found: C, 37.52; H, 6.73; N, 9.78; P, 5.41.

Optical rotation: $[\alpha]_D^{24} = +40.0°$ (c=0.60 in water) IR $\gamma_{max}^{KBr}$ cm$^{-1}$: 968.

Rf value was 0.55 on a thin layer chromatography using silica gel glass plate (Merck, Art.5721) in a solvent system which contained 5 parts by volume of the upper layer of $CHCl_3$: $CH_3OH$ : 28% ammonia: $H_2O$ (4:3:2:1) and 3 parts by volume of methanol, while that of free xylostasin employed as the control was 0.23.

For obtaining further accurate analytical values of the above product, it is acetylated to obtain tetra-N-acetylxylostasin-3'-phosphate dihydrate, which is subjected to elemental analysis.

Elemental analysis for $C_{25}H_{43}N_4O_{17}P \cdot 2H_2O$; Calcd. C, 40.65; H, 6.41; N, 7.59; P, 4.19; Found C, 40.95; H, 6.52; N, 7.70; P, 4.16.

REFERENCE EXAMPLE 3

Production of butirosin A-3'-phosphate

One hundred parts by volume of peptone medium (Trypticase Soy Broth; BBL(Division of Becton, Dickinson and company, Cockeysville, Md.)) is inoculated with *Bacillus Vitallinus* Z-1159(IFO-13296), and the medium is cultivated for 48 hours at 28° C. The seed culture is transfered into 3900 parts by volume of the said peptone medium, and the culture is incubated for 17 hours at 37° C. The culture broth is subjected to centrifugation to recover 23 parts of wet cells.

The wet cells are disrupted with 46 parts of alumina, and the disrupted cells are suspended in 138 parts by volume of 0.05M phosphate buffer (pH 7.5). The suspension is subjected to centrifuge to obtain 100 parts by volume of a crude enzyme solution.

To 100 parts by volume of the crude enzyme solution (protein amount 16 mg/milliliter) are added one part of butirosin A, 100 parts by volume of 0.5M phosphate buffer (pH 7.5), 20 parts by volume of 1M aqueous solution of magnesium acetate, 10 parts by volume of a 1M aqueous solution of 2-mercaptoethanol, 100 parts by volume of 2M aqueous solution of adenosinetriphosphate (pH 7.0). The whole is filled up to 1000 parts by volume with distilled water and kept standing at 37° C for 16 hours.

Reaction mixture is heated at 80° C for 5 minutes to cease the reaction, followed by centrifugation to remove the precipitate.

Thus obtained supernatant is run onto a column of 500 parts by volume of activated charcoal which have previously been treated by alkali. The column is washed with distilled water and eluted with 0.1N hydrochloric acid. The fractions containing butirosin A-3'-phosphate are collected and thereto is added 1000 parts by volume of anion-exchange resin (Amberlite IR-45, OH-form) to neutralize. The resin is removed by filtration and the mother liquor is concentrated under the reduced pressure. The concentrate is run onto a column of cation-exchange resin (200 parts by volume) (Amberlite CG-50, $NH_4^+$-form). The column is washed with distilled water and eluted with 0.3N aqueous ammonia. Fractions containing butirosin A-3'-phosphate are collected and concentrated under reduced pressure. The insolubles are removed by filtration and the filtrate is lyophilized, whereby 0.92 part of white powder (butirosin A-3'-phosphate) is obtained.

Elemental analysis $C_{21}H_{42}N_5O_{15}P \cdot 2H_2O$; Calcd.: C, 37.55; H, 6.90; N, 10.42; P, 4.61; Found; C, 37.73; H, 6.81; N, 10.09; P, 4.51.

Optical rotation: $[\alpha]_D^{24} + 29.5°$ (c=0.61, in water) IR $\gamma_{max}^{KBr}$ cm$^{-1}$: 1640, 973

REFERENCE EXAMPLE 4

Production of butirosin B-3'-phosphate

Two thousand parts by volume of an aqueous culture medium (pH 7.2) comprising 0.5% of glycerol, 0.5% of polypeptone, 0.5% of yeast extract and 0.3% of meat extract is inoculated with *Escherichia coli* Rll (IFO-13560). The medium is incubated at 37° C under aeration for 18 hours. The culture broth is subjected to centrifuge to recover 4.4 parts of wet cells. The cells are suspended into 17.6 parts by volume of 0.05M phosphate buffer (pH 7.0). The suspension is subjected to ultrasonic oscillation (Kaijo Denki Co., Ltd.; T-A-4201, 4280-type, 2A) to disintegrate the cells, followed by removing the debris(insoluble materials) by centrifugation, whereby 17 parts by volume of crude enzyme solution is obtained.

To 17 parts by volume of the crude enzyme solution are added 5 parts of butirosin B, 50 parts by volume of 0.5M phosphate buffer (pH 7.0), 100 parts by volume of 1M adenosine triphosphate solution, 50 parts by volume of 0.1M magnesium acetate solution and 50 parts by volume of 0.1M 2-mercapto ethanol, which is filled up to 500 parts by volume with distilled water. The mixture is subjected to enzymic reaction at 37° C for 20 hours.

The reaction mixture is heated at 80° C for 5 minutes to cease the reaction, followed by centrifugation. The supernatant is run onto a column of 100 parts by volume of cation-exchange resin [Amberlite IRC-50, $NH_4^+$-form]. The column is washed with water, and then eluted with 1N-aqueous ammonia to give fractions which contain butirosin B-3'-phosphate. The fractions are collected and concentrated under reduced pressure, and then the concentrate is run onto a column of 100 parts by volume of cation-exchange resin [carboxy-methyl Sephadex C-25, $NH_4^+$-form]. The column is washed with water, and eluted with 0.2N-aqueous ammonia to give fractions which contain butirosin B-3'-phosphate. The fractions are collected, concentrated and lyophilized, whereby 4.5 parts of butirosin B-3'-phosphate.

Elemental analysis: $C_{21}H_{42}N_5O_{15}P\cdot 2H_2O$; Calcd.: C, 37.55; H, 6.90; N, 10.42; P, 4.61; Found: C, 37.60; H, 6.91; N, 10.40; P, 4.78.

Optical rotation: $[\alpha]_D^{24}$ +38.8°(c=1, in water) IR $\gamma_{max}^{KBr}$ $cm^{-1}$: 1640, 975

REFERENCE EXAMPLE 5

Production of neomycin A-3'-phosphate

Neomycin A-3'-phosphate is prepared by the similar manner as described in Reference Example 4, causing the crude enzyme solution of *Escherichia coli* Rll (IFO-13560) to act upon neomycin A.

Elemental analysis: $C_{12}H_{26}O_9N_4P\cdot 3H_2O$; Calcd.: C, 31.65; H, 7.08; N, 12.30; P, 6.80; Found: C, 31.78; H, 7.22; N, 12.09; P, 6.81.

NMR($D_2O$) $\delta$ : 3.14(2-H), 4.01(3'-H), 5.78(1H,d,J=4Hz,1-H). IR $\gamma_{max}^{KBr}$ $cm^{-1}$: 965 Optical rotation: $[\alpha]_D^{27}$+95.17° (c=1.01, in water)

REFERENCE EXAMPLE 6

Production of kanamycin B-3'-phosphate

Kanamycin B-3'-phosphate is prepared by the similar manner as described in Reference Example 4, causing the crude enzyme solution of *Escherichia coli* Rll (IFO-13560) to act upon kanamycin B.

Elemental analysis: $C_{18}H_{38}N_5O_{13}P\cdot 3H_2O$; Calcd.: C, 35.00; H, 7.18; N, 11.34; P, 5.01; Found: C, 35.23; H, 7.06; N, 10.99; P, 5.06.

Optical rotation: $[\alpha]_D^{23}$+108.6°(c=0.53, in water) NMR ($\delta$ in $D_2O$): 4.36(3'-H, quartet), 5.18(1''-H, doublet), 5.78(1'-H, doublet). IR $\gamma_{max}^{KBr}$ $cm^{-1}$: 970(phosphate)

EXAMPLE 1

1. Production of 3'-chloro-3'-deoxyxylostasin and 2',3'-epimino-2'-deamino-3'-deoxyxylostasin:

A mixture of 0.1 part of xylostasin-3'-phosphate, 1 part by volume of 0,N-bis-trimethylsilylacetamide and 1 part by volume of trimethylchlorosilane is heated at 110° C for 24 hours. After the reaction, trimethylchlorosilane is removed by distillation under reduced pressure and 50 parts by volume of water and 30 parts by volume of methanol are added thereto. The whole mixture is stirred for 1 hour. pH of the mixture is adjusted to about 5 with sodium hydrogen carbonate. Methanol is removed by distillation. The resultant solution is run onto a column of 10 parts by volume of cation-exchange resin [Amberlite CG-50, $NH_4^+$-form]. The column is washed with 50 parts by volume of water, and then, fractionated by linear gradient method with 150 parts by volume of water and 150 parts by volume of 0.2N-aqueous ammonia, each fraction being five parts by weight.

From No.29 to 34 fractions 3'-chloro-3'-deoxyxylostasin dihydrate is recovered by concentration, No.36 to 45 fractions are collected and concentrated, to give 0.07 part of 2',3'-epimino-2'-deamino-3'-deoxyxylostasin.

a. Physico-chemical properties of 2',3'-epimino-2'-deamino-3'-deoxyxylostasin;

Elemental analysis: $C_{17}H_{32}N_4O_9\cdot 2H_2O$; Calcd. C, 43.21; H, 7.67; N, 11.85; Found C, 42.79; H, 6.90; N, 11.00.

Optical rotation: $[\alpha]_D^{23}$ + 44.3°(c=1.05, in water)

Mass spectrum: (measured as 0-trimethylsilyl-N-acetyl derivative) m/e 949 ($M^+$-15), 299

Rf value of thin-layer chromatography:

Plate: silica gel glass plate (manufactured by Marck & Co.)

Developing solvent systems: a mixture of (i) 5 parts by volume of the upper layer of chloroform-methanol-17% aqueous ammonia-water(4:3:2:1) and (ii) 3 parts by volume of methanol.

2',3'-epimino-2'-deamino-3'-deoxyxylostasin: 0.37
xylostasin: 0.33 b. Physico-chemical properties of 3'-chloro-3'-deoxyxylostasin dihydrate. Elemental analysis for $C_{17}H_{33}N_4O_8Cl\cdot 2H_2O$;

Calcd.: C, 40.12; H, 7.33; N, 11.01; Cl, 6.97; Found: C, 40.08; H, 7.29; N, 10.73; Cl, 6.55.

Optical rotation: $[\alpha]_D^{24}$=+29.7° (c=0.6 in water)

Rf value was 0.41 on a thin layer chromatography using silica gel glass plate (Art.5721, sold by Merck & Co.) in a solvent system which contained 5 parts by volume of the upper layer of $CHCl_3$: $CH_3OH$:aqueous ammonia:water (4:3:2:1) and 3 parts by volume of methanol, while that of free xylostasin employed as the control was 0.23.

2. Production of 3'-deoxyxylostasin from 2',3'-epimino-2'-deamino-3'-deoxyxylostasin:

In 20 parts by volume of water is dissolved 0.03 part of 2',3'-epimino-2'-deamino-3'-deoxyxylostasin, and in the presence of 0.35 part by volume of Raney nickel the mixture is stirred while introducing hydrogen gas at room temperature for 6 hours. After the reaction Raney nickel is removed by filtration. The Raney nickel is washed well with 1N aqueous ammonia and the washing is added to the filtrate and the whole is concentrated to about 20 parts by volume. The concentrate is run onto a column of 10 parts by volume of cation-exchange resin [Amberlite CG-50, $NH_4^+$-form]. The column is washed with 30 parts by volume of water, and then, fractionated by linear gradient method with 200 parts by volume of water and 200 parts by volume of aqueous ammonia, each fraction being five parts by volume.

From the No.43 to 58 fractions 0.019 part of 3'-deoxyxylostasin is recovered by concentration.

Elemental analysis: $C_{17}H_{34}N_4O_9\cdot H_2O$; Calcd. C, 44.73; H, 7.95; N, 12.27; Found C, 44.75; H, 7.87; N, 12.24.

Optical rotation: $[\alpha]_D^{24}$+28.0°(c=0.61, in water)

Rf value of thin-layer chromatography:

Developing solvent system: a mixture of (1) 5 parts by volume of the upper layer of chloroform-methanol-aqueous ammonia-water(4:3:2:1) and (2) 3 parts by volume of methanol.

3'-deoxyxylostasin: 0.26
Xylostasin: 0.23

3. Production of 3'-deoxyxylostasin from a mixture of 2',3'-epimino-2'-deamino-3'-deoxyxylostasin and 3'-chloro-3'-deoxyxylostasin:

A mixture of 0.1 part of 2',3'-epimino-2'-deamino 3'-deoxyxylostasin and 0.1 part of 3'-chloro-3'-deoxyxylostasin is subjected to reduction in the similar manner as the above Example 1-(2), whereby 0.13 part of 3'-deoxyxylostasin is obtained.

EXAMPLE 2

1. Production of 3'-chloro-3'-deoxybutirosin A and 2',3'-epimino-2'-deamino-3'-deoxybutirosin A:

A mixture of 0.1 part of butirosin A-3'-phosphate, 1 part by volume of N,O-bistrimethylsilylacetamide, 1 part by volume of trimethylchlorosilane and 1 part by volume of pyridine is heated at 110° C for 24 hours and then concentrated to dryness under reduced pressure, and to the concentrate are added 30 parts by volume of water and 10 parts by volume of methanol and the mixture is stirred for 1 hour. After adjusting the pH to about 5 the mixture is subjected to concentration to about 30 parts by volume under reduced pressure. The concentrate is run onto a column of 15 parts by volume of cation-exchange resin (Amberlite IRC-50, $NH_4^+$-form). The column is washed with water and eluted with 200 parts by volume of 2N-aqueous ammonia. The eluate is concentrated to the amount of about 20 parts by volume. The concentrate is run onto a column of 10 parts by volume of cation-exchange resin (Amberlite CG-50, $NH_4^+$-form). The column is washed with water, and then, fractionated by linear gradient method with 200 parts by volume of 0.1N aqueous ammonia and 200 parts by volume of 0.6N aqueous ammonia, each fraction being five parts by weight.

From No. 28 to 31 fractions 3'-chloro-3'-deoxybutirosin A is recovered by concentration. Upon concentration of No. 34 to 41 fractions 0.06 part of 2',3'-epimino-2'-deamino-3'-deoxybutirosin A is obtained.

a. Physio-chemical properties of 2',3'-epimino-2'-deamino-3'-deoxybutirosin A;

Elemental analysis: $C_{21}H_{39}N_5O_{11}.2H_2O$; Calcd: C, 43.97; H, 7.55;N, 12.20; Found: C, 43.42; H, 7.63; N, 11.88.

Optical rotation: $[\alpha]_D^{23}$ +25.3° (c=1.07, in water)

Rf value of thin-layer chromatography:

Plate: silica gel glass plate(manufactured by Merck & Co.)

Developing solvent system: methanol-water-15% aqueous solution of sodium chloride (9:1:5).

2',3'-epimino-2'-deamino-3'-deoxybutirosin A: 0.44

Butirosin A: 0.08 b. Physico-chemical properties of 3'-chloro-3'-deoxybutirosin A;

Elemental analysis: $C_{21}H_{40}N_5O_{11}Cl.2H_2O$; Calcd.: C, 41.34; N, 7.26; N, 11.47; Cl, 5.81; Found: C, 41.03; N, 7.31; N, 11.21; Cl, 5.60.

Optical rotation: $[\alpha]_D^{23}$ +21.3° (c=0.75, in water)

Rf value of thin-layer chromatography:

Plate: silica gel glass plate (manufactured by Merch & Co.)

Developing solvent system: upper layer of chloroform, methanol-17% aqueous ammonia-water(4:3:2:1).

3'-chloro-3'-deoxybutirosin A: 0.41

Butirosin A: 0.31

2. Production of 3'-deoxybutirosin A from 2', 3'-epimino-2'-deamino-3'-deoxybutirosin A:

In 20 parts by volume of water is dissolved 0.06 part of 2',3'-epimino-2'-deamino-3'-deoxybutirosin A, and in the presence of 1.5 parts by volume of Raney nickel the mixture is stirred while introducing hydrogen gas for 4.5 hours at 60° C. After the reaction Raney nickel is separated by filtration. The Raney nickel is washed well with 1N aqueous ammonia and the washing is added to the filtrate. The whole is concentrated to about 50 parts by volume. The concentrate is run onto a column of 40 parts by volume of cation-exchange resin [Amberlite CG-50, $NH_4^+$-form]. The column is washed with 150 parts by volume of water, and fractionated by linear gradient method with 750 parts by volume of water and 750 parts by volume of 1.0N aqueous ammonia, each fraction being fifteen parts.

From No. 50 to 71 fractions 0.042 part of 3'-deoxybutirosin A is recovered by concentration.

Elemental analysis: $C_{21}H_{41}N_5O_{11}.H_2O$; Calcd.: C, 45.23; H, 7.77; N, 12.55; Found: C, 44.98; H, 7.57; N, 12.37.

Optical rotation: $[\alpha]_D^{24}$ +24.4° (c=1.0, in water)

IR spectrum (KBr): 3370, 2935, 1650, 1580, 1345, 1100, 1026

Rf value of thin-layer chromatography:

Plate: silica gel glass plate (manufactured by Merck & Co.)

Developing solvent: upper layer of chloroform: methanol:17% aqueous ammonia: water(4:3:2:1)

3'-deoxybutirosin A: 0.32

Butirosin A: 0.31

3. Production of 3'-deoxybutirosin A from a mixture of 2',3'-epimino-2'-deamino-3'-deoxybutirosin A and 3'-chloro-3'-deoxybutirosin A:

A mixture of 0.05 part of 2', 3'-epimino-2'-deamino-3'-deoxybutirosin A and 0.05 part of 3'-chloro-3'-deoxybutirosin A is subjected to reduction in the similar manner as the above Example 2-(2), whereby 0.07 part of 3'-deoxybutirosin A is obtained.

EXAMPLE 3

Production of 2',3'-epimino-2'-deamino-3'-deoxybutirosin A:

A mixture of 0.05 part of butirosin A-3'-phosphate, 0.5 part by volume of O,N-bistrimethylsilylacetamide and 0.5 part by volume of hexamethylphosphoric acid triamide is treated in the same manner as Example 2, whereby 0.012 part of 2',3'-epimino-2'-deamino-3'-deoxybutirosin A is obtained.

EXAMPLE 4

1. Production of 2',3'-epimino-2'-deamino-3'-deoxybutirosin B and 3'-chloro-3'-deoxybutirosin B:

A mixture of 0.3 part of butirosin B-3'-phosphate, 3 parts by volume of bis(trimethyl)silylacetamide, 0.6 part by volume of trimethylchlorosilane, 0.6 part by volume of pyridine and 0.09 part of triphenylphosphine is heated at 110° C for 30 hours. After cooling the reaction mixture is subjected to concentration under reduced pressure. To the concentrate is added methanol to release the silyl groups. The methanol solution is concentrated to dryness under reduced pressure. To this concentrate is added 40 parts by volume of water, and the aqueous solution is extracted with 60 parts by volume of ethylacetate in twice. The water layer is run onto a column of 30 parts by volume of cation-exchange resin [Amberlite CG-50, $NH_4^+$-form]. The column is washed with water, and then, fractionated by linear gradient method with 450 parts by volume of 0.05N-aqueous ammonia and 450 parts by volume of 0.5N-aqueous ammonia, each fraction being one part by weight.

From No. 43 to 47 fractions 3'-chloro-3'-deoxybutirosin B is recovered by concentration. Upon concentration of No. 54 to 62 fractions 0.21 part of 2',3'-epimino-2'-deamino-3'-deoxy butirosin B is obtained.

a. Physico-chemical properties of 2',3'-epimino-2'-deamino-3'-deoxybutirosin B:

Elemental analysis: $C_{21}H_{39}N_5O_{11}.2H_2O$; Calcd.: C, 43.97; H, 7.55; N, 12.20; Found; C, 43.51; H, 7.29; N, 12.33.

Optical rotation: $[\alpha]_D^{24} + 36.9°$ (c=1.0, in water)

Rf value of thin-layer chromatography:

Plate silicagel glass plate (manufactured by Merck & Co.)

Developing solvent system: 15% aqueous solution of sodium chloride-methanol (5:3).

2',3'-epimino-2'-deamino-3'-deoxybutirosin B: 0.68 butirosin B: 0.32 b. Physico-chemical properties of 3'-chloro-3'-deoxybutirosin B:

Elemental analysis: $C_{21}H_{40}N_5O_{11}C_l.2H_2O$; Calcd.: C, 41.34; H, 7.26; N, 11.47; $C_l$, 5.81; Found: C, 40.98; H, 7.15; N, 11.31; Cl, 5.71.

Optical rotation: $[\alpha]_D^{24}$ +30.4° (c=0.7, in water)

Rf value of thin layer chromatography

Plate: silicagel glass plate (manufactured by Merck & Co.)

Developing solvent system: 15% aqueous solution of sodium chloride-methanol (5:3)

3'-chloro-3'-deoxybutirosin B: 0.49

Butirosin B: 0.32

2. Production of 3'-deoxybutirosin B from 2',-3'epimino-2'-deamino-3'-deoxybutirosin B:

In 300 parts by volume of water is dissolved 2 parts of 2', 3'-epimino-2'-deamino-3'-deoxybutirosin B, and in the presence of 10 parts of Raney-nickel the mixture is stirred while introducing hydrogen gas at 40° C for 7 hours at atmospheric pressure. After the reaction Raney nickel is separated by filtration. The Raney nickel is washed well with 1000 parts by volume of 1N-aqueous ammonia and the washing is added to the filtrate and the whole is concentrated to about 500 parts by volume. The concentrate is run onto a column of 250 parts by volume of cation-exchange resin [Amberlite CG-50, $NH_4^+$-form]. The column is washed with 500 parts by volume of water, and fractionated by linear gradient method with 1200 parts by volume of 0.3N-aqueous ammonia and 1200 parts by volume of 0.7N-aqueous ammonia, each fraction being sixteen parts by weight.

Upon concentration of No. 113 to 134 fractions 1.2 parts of 3'-deoxybutirosin B is obtained.

Elemental analysis: $C_{21}H_{41}N_5O_{11}.H_2O$; Calcd.; C, 45.23; H, 7.77; N, 12.55; Found; C, 45.62; H, 7.92; N, 12.22.

Optical rotation: $[\alpha]_D^{24}$ +35° (c=1, in water)

3. Production of 3'-deoxybutirosin B from 2', 3'-epimino-2'-deamino-3'-deoxybutirosin B and 3'-chloro-3'-deoxybutirosin B:

A mixture of 1 part of 2',3'-epimino-2'-deamino-3'-deoxybutirosin B and 1 part of 3'-chloro-3'-deoxybutirosin B is subjected to reduction in the similar manner as Example 4-(2), whereby 1.4 part of 3'-deoxybutirosin B is obtained.

EXAMPLE 5

1. Production of 3'-chloro-3'-deoxybutirosin A:

A mixture of 1 part of butirosin A-3'-phosphate, 10 parts by volume of N,O-bis(trimethylsilyl)acetamide and 5 parts by volume of trimethylchlorosilane is heated at 110° C for 24 hours. After the reaction the reactions system is cooled, and trimethylchlorosilane is removed by evaporation. To the residue are added 100 parts by volume of water and 50 parts by volume of methanol. The mixture is stirred at room temperature for 1 hours. After the pH of the mixture is adjusted to about 5.5 with $NaHCO_3$, and concentrated to remove methanol under reduced pressure. The concentrate is run onto a column of 100 parts by volume of cation-exchange resin [Amberlite IRC-50, $NH_4^+$-form, manufactured by Rohm and Haas, Co.]. The column is washed with 500 parts by volume of water, and then, the column is eluted with 500 parts by volume of 1N-aqueous ammonia. The eluate is concentrated under reduced pressure to about 50 parts by volume.

The concentrate is run onto a column of 40 parts by volume of cation-exchange resin [Amberlite CG-50, $NH_4^+$-form]. The column is fractionated by the linear gradient method by 600 parts by volume of water and 600 parts by volume of 0.5N aqueous ammonia, each fraction being ten part by weight.

Upon concentration of No. 55 to 68 fractions 0.22 part of 3'-chloro-3'-deoxybutirosin A is obtained.

Elemental analysis: $C_{21}H_{40}N_5O_{11}Cl.2H_2O$; Calcd.: C, 41.34; H, 7.26; N, 11.47; Cl, 5.81; Found: C, 41.03; H, 7.31; N, 11.21; Cl, 5.60.

Optical rotation: $[\alpha]_D^{23}$ +21.3° (c=0.75, in water)

Rf value of thin-layer chromatography:

Plate: silica gel glass plate (manufactured by Merck & Co.)

Developing solvent system: upper layer of chloroform-methanol-17% aqueous ammonia-water(4:3:2:1).

3'-chloro-3'-deoxybutirosin A: 0.41 Butirosin A: 0.31

2. Production of 3'-deoxybutirosin A from 3'-chloro-3'-deoxybutirosin A:

In 0.05 part by volume of triethylamine and 10 parts by volume of $H_2O$ is dissolved 0.1 part of 3'-chloro-3'-deoxybutirosin A, and in the presence of 1 part by volume of Raney nickel the mixture is stirred while introducing hydrogen gas at atmospheric pressure at room temperature for 4.5 hours. After the reaction Raney nickel is recovered by filtration. The Raney nickel is washed well with 100 parts by volume of 1N-aqueous ammonia, and the washing is added to the filtrate. The whole is concentrated under reduced pressure to about 20 parts by volume.

The concentrate is run onto a column of 40 parts by volume of cation-exchange resin [Amberlite CG-50, $NH_4^+$-form]. The column is washed with 500 parts by volume of water, and fractionated by linear gradient method with 600 parts by volume of 0.3N aqueous ammonia and 600 parts by volume of 1N aqueous ammonia, each fraction being ten parts by weight.

Upon concentration and lyophilization of No. 48 to 70 fraction 0.063 part of 3'-deoxybutirosin A is obtained.

Elemental analysis: $C_{21}H_{41}N_5O_{11}.H_2O$; Calcd.: C, 45.23; H, 7.77; N, 12.55; Found: C, 44.98; H, 7.57; 12.37.

Optical rotation: $[\alpha]_D^{24}$ +24.4° (c=1.0 in water)

IR spectrum (KBr): 3370, 2935, 1650, 1580, 1345, 1100, 1026

Rf value of thin-layer chromatography:

Plate: silica gel G glass plate(manufactured by Merck & Co.)

Developing solvent system: upper layer of chloroformmethanol-17% aqueous ammonia-water(4:3:2:1).

3'-deoxybutirosin A: 0.32

Butirosin A: 0.31

EXAMPLE 6

1. Production of 2',3'-epimino-2'-deamino-3'-deoxyneomycin A:

A solution of 3 parts of neomycin A-3'-phosphate, 30 parts by volume of hexamethyldisilazane, 30 parts by volume of hexamethylphosphoric triamide is heated at 120° C for 66 hours. After cooling, 100 parts by volume of water is added thereto, After the pH of the mixture is adjust to about 5.0 with acetic acid, the mixture is stirred for one hour. The resultant solution is run onto a column of 150 parts by volume of cation-exchange resin [Amberlite CG-50, $NH_4^+$-form]. The column is washed with 500 parts by volume of water, and fractionated by linear gradient method with 1200 parts by volume of water and 1200 parts by volume of 0.3N-aqueous ammonia, and then with 0.3N-aqueous ammonia, each fraction being 12 parts by weight.

Upon concentration of No. 180 to 280 fractions 1.05 part of 2', 3'-epimino-2'-deamino-3'-deoxyneomycin A is obtained.

a. Physico-chemical properties of 2',3'-epimino-2'-deamino-3'-deoxyneomycin A:

Rf value of thin-layer chromatography:
Plate; silica gel glass plate (manufactured by Merck & Co.)
Developing solvent: upper layer [of chloroformmethanol-aqueous ammonia-water(4:3:2:1)]-methanol (5:3)
2',3'-epimino-2'-deamino-3'-deoxyneomycin A: 0.27
Neomycin A: 0.30
Mass spectrum: (measured as O-trimethylsilyl, N-acetyl derivative) m/e 673 ($M^+$-15)

2. Production of 3'-deoxyneomycin A from 2',3'-epimino-2'-deamino-3'-deoxyneomycin A:

In 50 parts by volume of water is dissolved 0.3 part of 2',3'-epimino-2'-deamino-3'-deoxyneomycin A, and in the presence of 3 parts by volume of Raney nickel the mixture is stirred while introducing hydrogen gas at a pressure of 100 kg/cm³ at 60° C for 5 hours. After reaction Raney nickel is separated by filtration. The Raney nickel is washed well with 100 parts by volume of 1N-aqueous ammonia, and the washing is added to the filtration. The whole is concentrated to about 50 parts by volume. After the pH of the concentrate is adjusted to about 5.0 with hydrochloric acid, the mixture is run onto a column of 40 parts by volume of cation-exchange resin [Amberlite CG-50, $NH_4^+$-form].

The column is washed with 100 parts by volume of water, and fractionated by linear gradient method with 300 parts by volume of 0.4N-aqueous ammonia and 300 parts by volume of 0.6N-aqueous ammonia, each fraction being 10 parts by weight. From No. 23 to 39 fractions 0.17 part of 3'-deoxyneomycin A is obtained.

Physico-chemical properties of 3'-deoxyneomycin A:
Optical rotation: $[\alpha]_D^{24}$ +75.6° (c=0.94, in water)
Mass spectrum: (measured as O-trimethylsilyl, N-acetyl derivative) 690 ($M^+$), 675($M^+$-15), 301
Rf value of thin-layer chromatography:
Plate: silica gel glass plate (manufactured by Merck & Co.)
Developing solvent: upper layer[of chloroformmethanol-aqueous ammonia-water(4:3:2:1)]-methanol(5:3)
3'-deoxyneomycin A: 0.38
Neomycin A: 0.30

EXAMPLE 7

1. Production of 2',3'-epimino-2'-deamino-3'-deoxy kanamycin B:

A solution of one part of kanamycin B-3'-phosphate, 10 parts by volume of bis(trimethylsilyl)acetamide, 2 parts by volume of trimethylchlorosilane and 0.4 part of triphenylphosphine is heated at 115° C for 30 hours. After cooling, the reaction mixture is concentrated under reduced pressure, and to the concentrate is added 100 parts by volume of methanol and 50 parts by volume of water, and then the mixture is stirred for one hour. Methanol is removed by distillation, and ethyl acetate-soluble portion is removed. The water layer is run onto a column of 60 parts by volume of cation-exchange resin [Amberlite CG-50, $NH_4^+$-form]. The column is washed with 200 parts by volume of water, and fractionated by linear gradient method with 600 parts by volume of water and 600 parts by volume of 0.5N-aqueous ammonia, each fraction being 10 parts by weight.

From No. 24 to 34 fractions 3'-chloro-3'-deoxykanamycin B is recovered by concentration. Upon concentration of No. 55 to 80 fractions 0.61 part of 2',3'-epimino-2'-deamino-3'-deoxykanamycin B is obtained.

a. Physicochemical properties of 2',3'-epimino-2'-deamino-3'-deoxykanamycin B;

Rf value of thin layer chromatography:
Plate: silica gel glass plate (manufactured by Merck & Co.)
Developing solvent: upper layer of chloroform-methanol-17%-aqueous ammonia (2:1:1)
2',3'-epimino-2'-deamino-3'-deoxykanamycin B: 0.70
Kanamycin B: 0.78 b. Physico-chemical properties of 3'-chloro-3'-deoxykanamycin B:

Rf value of thin layer chromatography:
Plate: silica gel glass plate (manufactured by Merck) & Co.)
Developing solvent: upper later [of chloroform-methanol-water-aqueous ammonia (2.0:1.5:0.5:1.0)]-methanol (1:1)
3'-chloro-3'-deoxykanamycin B: 0.55
Kanamycin B: 0.39

2. Production of 3'-deoxykanamycin B from 2', 3'-epimino-2'-deamino-3'-deoxykanamycin B:

In 40 parts by volume of water is dissolved 0.6 part of 2', 3'-epimino-2'-deamino-3'-deoxykanamycin B, and in the presence of 9 parts by volume of Raney nickel the mixture is stirred while introducing hydrogen gas at a pressure of 100 kg/cm² at 60° C for 6 hours. After the reaction Raney nickel is separated by filtration. The Raney nickel is washed well with 300 parts by volume of 1N-aqueous ammonia and the washing is added to the filtrate. The whole is concentrated to about 100 parts by volume. The precipitated insolubles are removed by filtration, and the pH of the supernatant is adjusted to about 5.0 with hydrochloric acid. The mixture is run onto a column of 50 ml. of cation-exchange resin [Amberlite CG-50, $NH_4^+$-form].

The column is washed with 150 parts by volume of water, and fractionated by linear gradient method with 1400 parts by volume of water and 1400 parts by volume of 0.3N-aqueous ammonia, each fraction being 14 parts by weight. From No. 146 to 162 fractions 0.30 part of 3'-deoxykanamycin B is obtained.

Elemental analysis: $C_{18}H_{37}N_5O_9 \cdot 2H_2O$; Calcd.: C, 42.93; H, 8.20; N, 13.90; Found: C, 42.11; H, 8.04; N, 13.05.

Optical rotation: $[\alpha]_D^{23} +123.2°$ (c=1.085, in water)

Rf value of thin-layer chromatography:
Plate: silica gel glass plate (manufactured by Merck & Co.)
Developing solvent: upper layer of chloroformmethanol-17% aqueous ammonia (2:1:1)
3'-deoxykanamycin B: 0.74
3'-chloro-3'-deoxykanamycin B: 0.78

3. Production of 3'-deoxykanamycin B from a mixture of 2',3'-epimino-2'-deamino-3'-deoxykanamycin B and 3'-chloro-3'-deoxykanamycin B:

A mixture of 0.5 part of 2',3'-epimino-2'-deamino-3'-deoxykanamycin B and 0.5 part of 3'-chloro-3'-deoxykanamycin B is subjected to reduction in the similar manner as Example 7-(2), whereby 0.65 part of 3'-deoxykanamycin B is obtained.

What we claim is:

1. A method for the production of a deoxyaminoglycoside antibiotic selected from the group consisting of (1) 3'-and/or 5''-deoxyneomycin and (2) 3'-and/or 2''-deoxykanamycin antibiotics, which comprise reacting the corresponding phosphorylated aminoglycode with a silylating agent selected from the group consisting of halosilanes, silyl compounds of amines, bissilyl compounds of carboxylic acid amides, monosilyl compounds of carboxylic acid amides, silyl derivatives of imidazole, a mixture of a trialkylsilane and a metal catalyst, and a mixture of a dialkyarylsilane and a metal catalyst, and subjecting the thus obtained intermediate to catalytic reduction, electrolytic reduction, reduction with a reducing agent or reduction with a Grignard reagent.

2. A method for the production of deoxybutirosin A or deoxybutirosin B which comprises reacting the corresponding 3'-and/or 5''-phosphorylated aminoglycoside with (i) a silylating agent selected from the group consisting of hexamethyldisilazane, trimethylchlorosilane, bis(trimethylsilyl)acetamide, bis(trimethylsilyl)-trifluoroacetamide, trimethylsilylacetamide, N-methyl-N-trimethylsilylacetamide, N-trimethylsilylimidazole, N-(trimethylsilyl) diethylamine and halosilanes, or acylating agent selected from the group consisting of acetic anhydride, acetyl chloride and benzoyl chloride, and (ii) a halogenating agent selected from the group consisting of trialkylsilyl halides, triarylsilyl halides, arylalkylsilyl halides, trialkoxysilyl halides, thionyl chloride, trimethoxymethylphosphonium iodide, phosphorus oxychloride, phosphorus thiooxychloride, phosphorus pentachloride, oxalyl chloride and phosphorus pentabromide, and subjecting the thus obtained intermediate to catalytic reduction, electrolytic reduction, reduction with a reducing agent or reduction with a Grignard reagent.

3. A method according to claim 1, wherein the intermediate is the corresponding epiminodeaminodeoxyaminoglycoside.

4. A method according to claim 2, wherein the intermediate is the corresponding halogenodeoxybutirosin.

5. An epiminodeaminodeoxyaminoglycoside antibiotic compound selected from the group consisting of 2',3'-epimino-2'-deamino-3'-deoxyxylostasin, 2',3'-epimino-2'-deamino-3'-deoxybutirosin A, 2',3'-epimino-2'-deamino-3'-deoxybutirosin B, 2',3'-epimino-2'-deamino-3'-deoxyneomycin A, 2',3'-epimino-2'-deamino-3'-deoxykanamycin B and pharmaceutically acceptable salts thereof.

6. A compound as claimed in claim 5, wherein the compound is 2',3'-epimino-2'-deamino-3'-deoxyxylostasin.

7. A compound as claimed in claim 5, wherein the compound is 2',3'-epimino-2'-deamino-3'-deoxybutirosin A.

8. A compound as claimed in claim 5, wherein the compound is 2', 3'-epimino-2'-deamino-3'-deoxybutirosin B.

9. A compound as claimed in claim 5, wherein the compound is 2',3'-epimino-2'-deamino-3'-deoxyneomycin A.

10. A compound as claimed in claim 5, wherein the compound is 2',3'-epimino-2'-deamino-3'-deoxykanamycin B.

11. 3'-chloro-3'-deoxybutirosin A or a pharmaceutically acceptable salt thereof.

12. 3'-chloro-3'-deoxybutirosin B or a pharmaceutically acceptable salt thereof.

* * * * *